(12) United States Patent
Flynn

(10) Patent No.: US 7,635,067 B1
(45) Date of Patent: Dec. 22, 2009

(54) GLOVE DISPENSING SYSTEM

(76) Inventor: William Flynn, 20 W. Main St., Apt. 2R, Westborough, MA (US) 01581

( * ) Notice: Subject to any disclaimer, the term of this patent is extended or adjusted under 35 U.S.C. 154(b) by 0 days.

(21) Appl. No.: 11/803,045

(22) Filed: May 11, 2007

Related U.S. Application Data

(60) Provisional application No. 60/800,506, filed on May 15, 2006.

(51) Int. Cl.
*B65H 1/00* (2006.01)
(52) U.S. Cl. .................... 221/45; 221/46; 221/221; 221/224; 221/93; 223/111
(58) Field of Classification Search ......... 221/1–312 C; 700/231–244; 223/111
See application file for complete search history.

(56) References Cited

U.S. PATENT DOCUMENTS

| | | | | |
|---|---|---|---|---|
| 5,456,354 A * | 10/1995 | Wood | ............................ | 206/278 |
| 5,584,390 A * | 12/1996 | Wood | ............................ | 206/278 |
| 5,816,440 A | 10/1998 | Shields et al. | .................. | 221/45 |
| 5,878,909 A * | 3/1999 | Rogow | ........................... | 221/45 |
| 5,921,434 A | 7/1999 | Hollander et al. | .............. | 221/34 |
| 5,927,543 A * | 7/1999 | Dejardin et al. | ................ | 221/56 |
| 6,053,380 A * | 4/2000 | Sherrod | ........................ | 223/111 |
| 6,375,034 B1 | 4/2002 | Corbett | .......................... | 221/46 |
| 6,637,035 B1 * | 10/2003 | Brinkmann et al. | ........... | 2/161.6 |
| 2005/0155133 A1 * | 7/2005 | Sato | ................................ | 2/159 |
| 2006/0010563 A1 | 1/2006 | Michel et al. | .................... | 2/159 |
| 2006/0144878 A1 * | 7/2006 | Williams | ....................... | 223/111 |

* cited by examiner

*Primary Examiner*—Gene Crawford
*Assistant Examiner*—Michael K Collins

(57) ABSTRACT

A glove dispensing system includes glove bearing sheets and a glove opening mechanism. In use, the glove dispensing system opens a cuff end of the gloves carried by the glove bearing sheets and presents the open gloves to a user. As such, the glove dispensing system provides the user with a substantially sterile glove in a manner that allows the user to easily don the gloves while limiting a risk of the user contaminating an exterior surface of the glove by touching with his hands or other body parts. In one arrangement, the gloves are integrally formed as part of the glove bearing sheets, such as by a heat-sealing process. The gloves can include coupling mechanism that secures the gloves to the glove bearing sheets and that allows ease of removal of the gloves from the glove bearing sheets after being donned by the user by a user.

18 Claims, 6 Drawing Sheets

GLOVE DISPENSING SYSTEM

CROSS REFERENCE TO RELATED APPLICATIONS

This Patent Application claims benefit of U.S. Patent Application No. 60/800,506 filed on May 15, 2006, entitled, "GLOVE SYSTEM", the contents and teachings of which are hereby incorporated by reference in their entirety.

BACKGROUND

Individuals in the health care or food service industry regularly don disposable gloves in order to prevent the transmission of bacteria or other contaminants to themselves and to others. In certain cases, the disposable gloves are contained within, and dispensed from, a cardboard box. When donning a pair of gloves dispensed in this manner, a user typically grasps a glove and pulls the glove from the box using an uncovered hand. Once removed from the box, the user places the glove onto one of his uncovered hands. The user can then use his now covered hand to grasp and remove a second glove from the box and then place the second glove upon his ungloved hand.

SUMMARY

Conventional disposable glove dispensers suffer from a variety of deficiencies. For example, with the dispenser box described above, the gloves are stored in a generally clean and antiseptic state. However, the dispenser box requires that a user remove a first glove from the glove dispenser using an ungloved hand. As such, the first glove donned by the user can be contaminated by the ungloved hand of the user. Furthermore, as the user uses this potentially soiled glove to grasp and remove the second glove in order to don it, the user can potentially contaminate the second glove as well. As a result of contaminating the previously sterile gloves dispensed by the dispenser box, the user can transmit infections, diseases, or other contaminants to either patients in a healthcare setting or customer in a food services setting.

By contrast to conventional glove dispensers, embodiments of the present invention relate to a system for dispensing gloves, such as disposable polymer or latex film gloves of the type used in the food service industry and the health care industry. The glove dispensing system includes glove bearing sheets and a glove opening mechanism. In use, the glove dispensing system opens a cuff end of the gloves carried by the glove bearing sheets and presents the open gloves to a user. As such, the glove dispensing system provides the user with a substantially sterile glove in a manner that allows the user to easily don the gloves while limiting a risk of the user contaminating an exterior surface of the glove by touching with his hands or other body parts. In one arrangement, the gloves are integrally formed as part of the glove bearing sheets, such as by a heat-sealing process. The gloves include coupling mechanism, such as a series of perforations extending about the outer periphery of the glove, that secures the gloves to the glove bearing sheets and that allows ease of removal of the gloves from the glove bearing sheets after being donned by the user by a user.

In one arrangement, a glove dispensing system includes a housing, a glove bearing sheet carried by the housing, and a glove opening mechanism coupled to the housing. The glove bearing sheet includes a first sheet portion and a second sheet portion, the first sheet portion overlying the second sheet portion. The first sheet portion defines a first leading edge at a first end of the glove bearing sheet and the second sheet portion defining a second leading edge at the first end of the glove bearing sheet, and the first and second sheet portions defining a trailing edge at a second end of the glove bearing sheet, the first end of the glove bearing sheet opposing the second end of the glove bearing sheet. The glove bearing sheet includes a glove carried by the glove bearing sheet between the first and second leading edges and the trailing edge such that a cuff portion of the glove is disposed in proximity to the first and second leading edges and such that fingertip portions of the glove extend toward the trailing edge, the glove being removeably attached to the glove bearing sheet. The glove opening mechanism coupled is constructed and arranged to (i) receive the first and second leading edges of the glove bearing sheet and position the first and second leading edges of the glove bearing sheet from a substantially closed position to a substantially open position to open at least the cuff portion of the glove and (ii) receive the trailing edge of the glove bearing sheet to maintain and support the glove bearing sheet within the glove dispensing system.

In one arrangement, a glove bearing sheet includes a first sheet portion and a second sheet portion, the first sheet portion overlying the second sheet portion. The first sheet portion defines a first leading edge at a first end of the glove bearing sheet, the second sheet portion defining a second leading edge at the first end of the glove bearing sheet, and the first and second sheet portions defining a trailing edge at a second end of the glove bearing sheet, the first end of the glove bearing sheet opposing the second end of the glove bearing sheet. The glove bearing sheet includes a glove integrally and removeably formed as part of the first sheet portion and the second sheet portion of the glove bearing sheet between the first and second leading edges and the trailing edge. A cuff portion of the glove is disposed in proximity to the first and second leading edges with the fingertip portions of the glove extending toward the trailing edge.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Embodiments of the present invention relate to a system for dispensing gloves, such as disposable polymer or latex film gloves of the type used in the food service industry and the health care industry. The glove dispensing system includes glove bearing sheets and a glove opening mechanism. In use, the glove dispensing system opens a cuff end of the gloves carried by the glove bearing sheets and presents the open gloves to a user. As such, the glove dispensing system provides the user with a substantially sterile glove in a manner that allows the user to easily don the gloves while limiting a risk of the user contaminating an exterior surface of the glove by touching with his hands or other body parts. In one arrangement, the gloves are integrally formed as part of the glove bearing sheets, such as by a heat-sealing process. The gloves include coupling mechanism, such as a series of perforations extending about the outer periphery of the glove, that secures the gloves to the glove bearing sheets and that allows ease of removal of the gloves from the glove bearing sheets after being donned by the user by a user.

Referring to FIGS. 1-4, an embodiment of a glove dispensing system 5 is shown. The glove dispensing system 5 includes one or more glove bearing sheets 42 carried by a glove dispenser 10.

Figure 5:
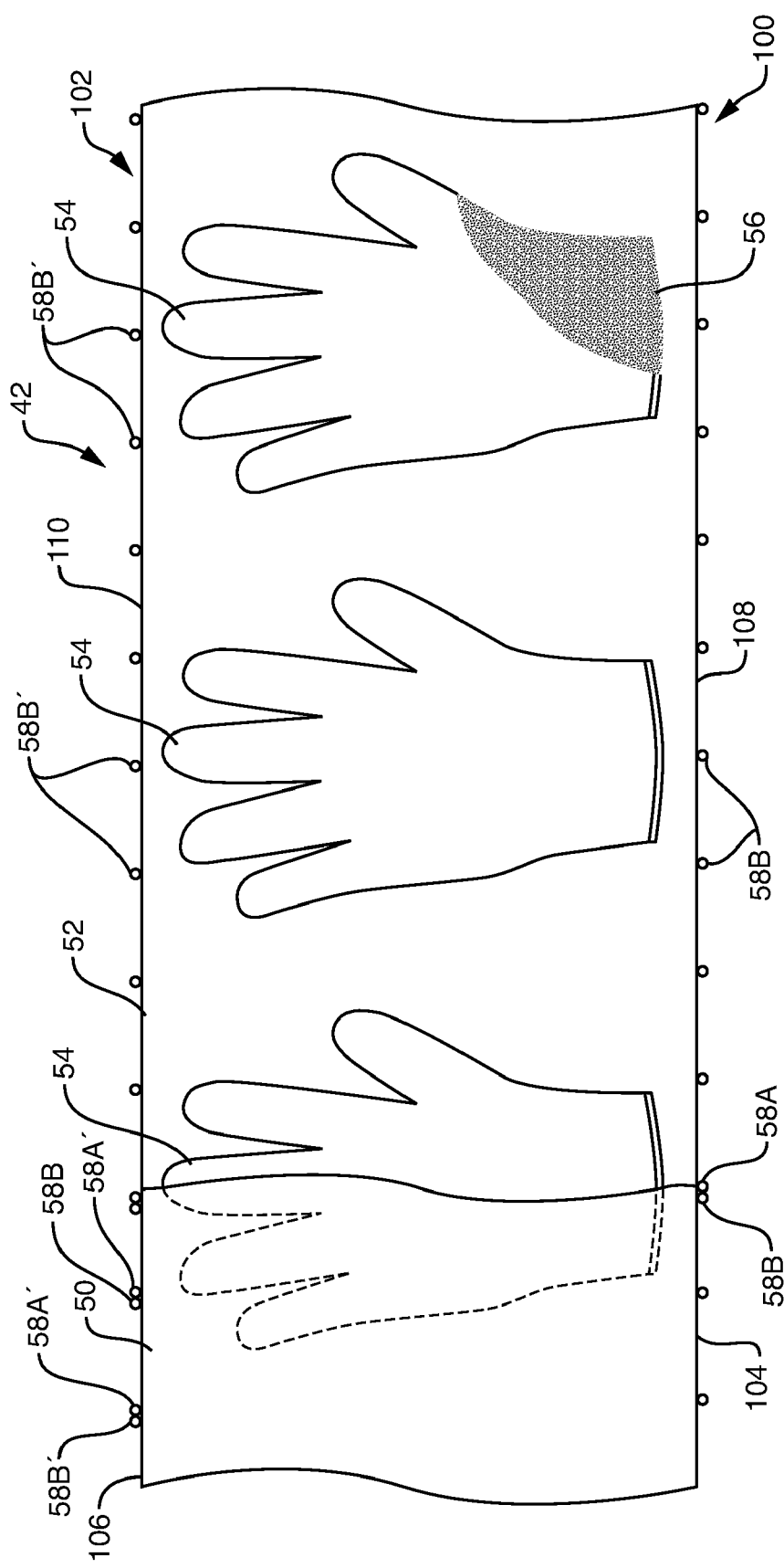
FIG. 5 is a fragmentary plan view of a section of an embodiment of glove bearing sheet adapted for use on the dispenser of FIG. 1.

FIG. 5 illustrates an embodiment of a glove bearing sheet 42 carried by the glove dispensing system 5. As illustrated, the glove bearing sheet 42 includes a plurality of spaced gloves 54, such as formed from a plastic or latex material, disposed between a first sheet portion (e.g. inner sheet) 50 and a second sheet portion (e.g., outer sheet) 52. The first sheet portion 50 of the glove bearing sheet 42 has a first leading edge 104 that includes a protrusion, such as beads 58A, at a first end 100 of the glove bearing sheet 42 and a first trailing edge 106 that includes a protrusion, such as beads 58A', at a second end 102 of the glove bearing sheet 42. The second sheet portion 52 of the glove bearing sheet 42 includes a second leading edge 108 that includes a protrusion, such as beads 58B, at the first end 100 of the glove bearing sheet 42 and a second trailing edge 110 that includes a protrusion, such as beads 58B', at a second end 102 of the glove bearing sheet 42. The beads 58A, 58A' are disposed on the first sheet portion 50 slightly ahead of the beads 58B, 58B' disposed on the second sheet portion 52 such that, when the glove bearing sheet 42 is installed on the glove dispenser 10, beads 58A, 58A', 58B, and 58B' lie in substantially the same plane on the glove bearing sheet 42.

Each glove 54 is releasably connected to the first and second sheet portions 50, 52, such as by adhesive 56 for example. The adhesive 56 is firmly fixed to the sheets 50 and 52. The gloves 54 stick to the adhesive 56 sufficiently to enable the gloves 54 to be opened when the outer sheet 50 is separated from the inner sheet 52 by the glove dispenser 10, as will be described below. In one arrangement, the glove bearing sheet 42 is rolled about a tubular core 46 to support the glove bearing sheet 42 once disposed within the glove dispenser.

In one arrangement, the glove dispenser 10 includes a housing 12 having a glove sheet support assembly 29, a glove sheet advancement mechanism 35, a glove sheet receiver assembly 31, and a glove opening mechanism 60.

The glove sheet support assembly 29 is configured to carry a first glove bearing sheet 42 and a second glove bearing sheet 42' and to allow rotation of the glove bearing sheets 42, 42' relative to the housing 12. In one arrangement the glove bearing sheet assembly 29 is disposed on an upper surface 17 of the housing 12 and includes first and second shafts 34, 34' that are mounted to a corresponding first rear flange 22. For example, a first end of each shaft 34, 34' are secured within corresponding apertures 37, 37' defined by the first rear flange 22. Opposite second ends of shafts 34, 34' extend into corresponding apertures 38, 38' defined in a first front flange 14. The apertures 38, 38' are sized to provide sufficient clearance, relative to the second ends of the shafts 34, 34', to allow the upper front flange 14 to be pivoted into and out of engagement with the second ends of the shafts 34, 34'.

In one arrangement, the upper front flange 14 is pivotally connected to the upper surface 17 by a hinge 18 to allow for pivotal movement of the upper front flange 14 relative to the housing. Such pivotal movement allows a user to insert glove bearing sheets 42 onto, or remove the glove bearing sheets 42 from, the shafts 34, 34' of the glove bearing sheet support assembly 29.

Each shaft 34, 34' includes upper spindles 30, 30' that are adapted to receive a glove bearing sheet 42, such as a glove bearing sheet 42 disposed about a tubular core 46. Each spindle 30, 30' is selectively rotated by the glove sheet advancement mechanism 35. The glove sheet advancement mechanism 35, such as a motor, is constructed and arranged to advance the sheet assembly of each glove bearing sheet 42 through the glove opening mechanism 60 to present a glove 54 on the glove bearing sheet 42 in an open configuration to a user. In one arrangement, once a user has removed a glove from the glove bearing sheet, the glove sheet advancement mechanism 35 is constructed and arranged to advance spent glove bearing sheet 42 onto the glove sheet receiver assembly 31. In one arrangement, the glove sheet advancement mechanism 35 can be energized by a remote electrical switch, not shown, or can be manually actuated.

In one arrangement, the glove sheet receiver assembly 31 is configured to receive the remnants of the glove bearing sheet 42 (e.g., the first and second sheets 50, 52) once a user has removed a glove 54 from the glove bearing sheet 42. For example, the glove sheet receiver assembly 31 is disposed on a lower surface 19 of the housing 12 and includes a pair of lower spindles 32, 32' fixed to a pair of shafts 36, 36' that are, in turn, mounted for axial rotation on a front lower flange 16 and a rear lower flange 24. A first end of each shaft 36, 36' extends into corresponding apertures 39 defined by the rear lower flange 24 while opposing second ends of shafts 36, 36' extend into corresponding apertures 40 defined by the front lower flange 16. The apertures 40, 40' are sized to provide sufficient clearance, relative to the second ends of the shafts 36, 36', to allow the lower front flange 16 to be pivoted into and out of engagement with the second ends of the shafts 36, 36'. In one arrangement, receiver cores 48, 48' are disposed on corresponding lower spindles 32, 32' and are each configured to roll the spent glove bearing sheets 42 received from the glove opening mechanism into a generally tubular and compact shape.

Figure 2:
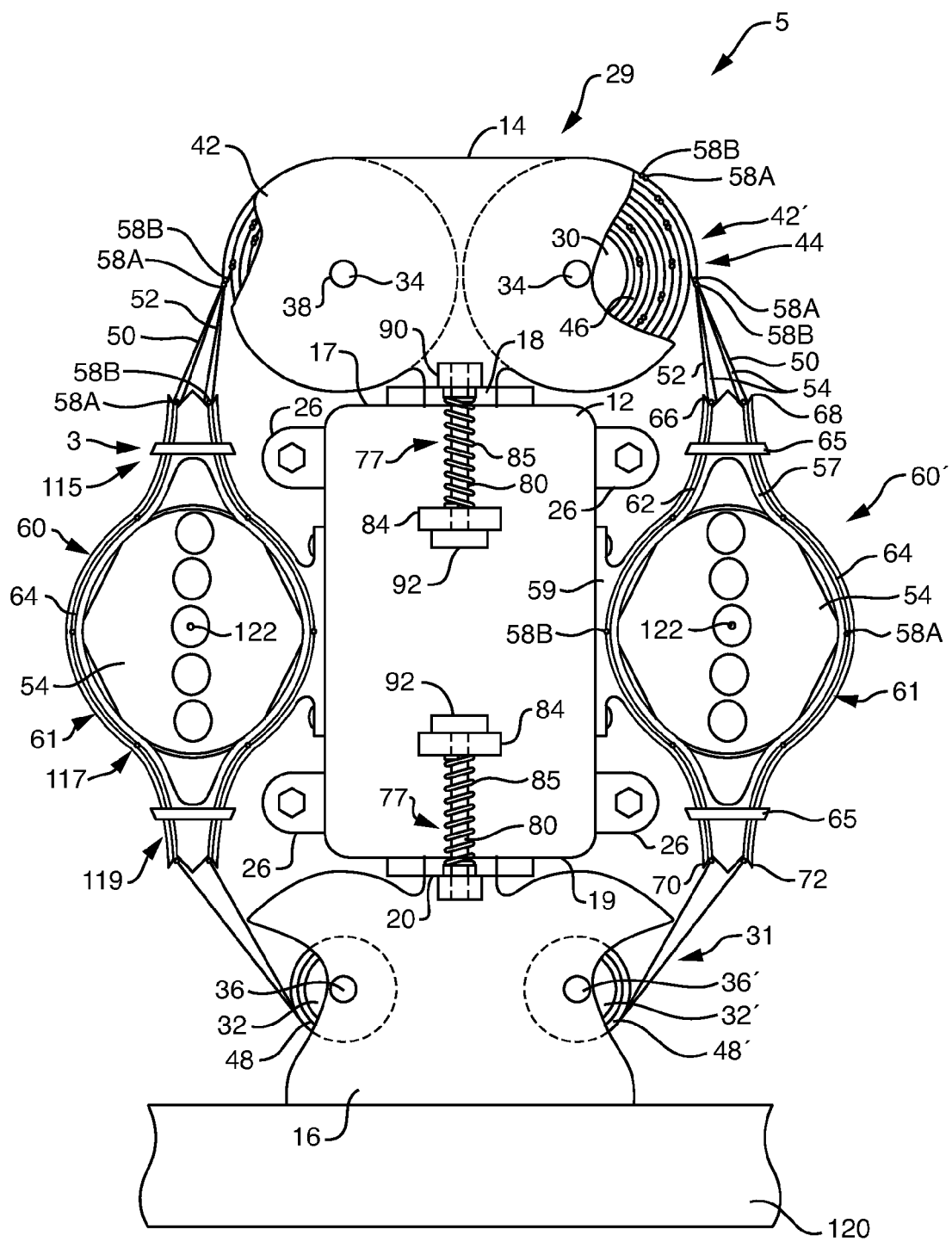
FIG. 2 is a front elevational view of the glove dispenser system of FIG. 1.
Figure 3:
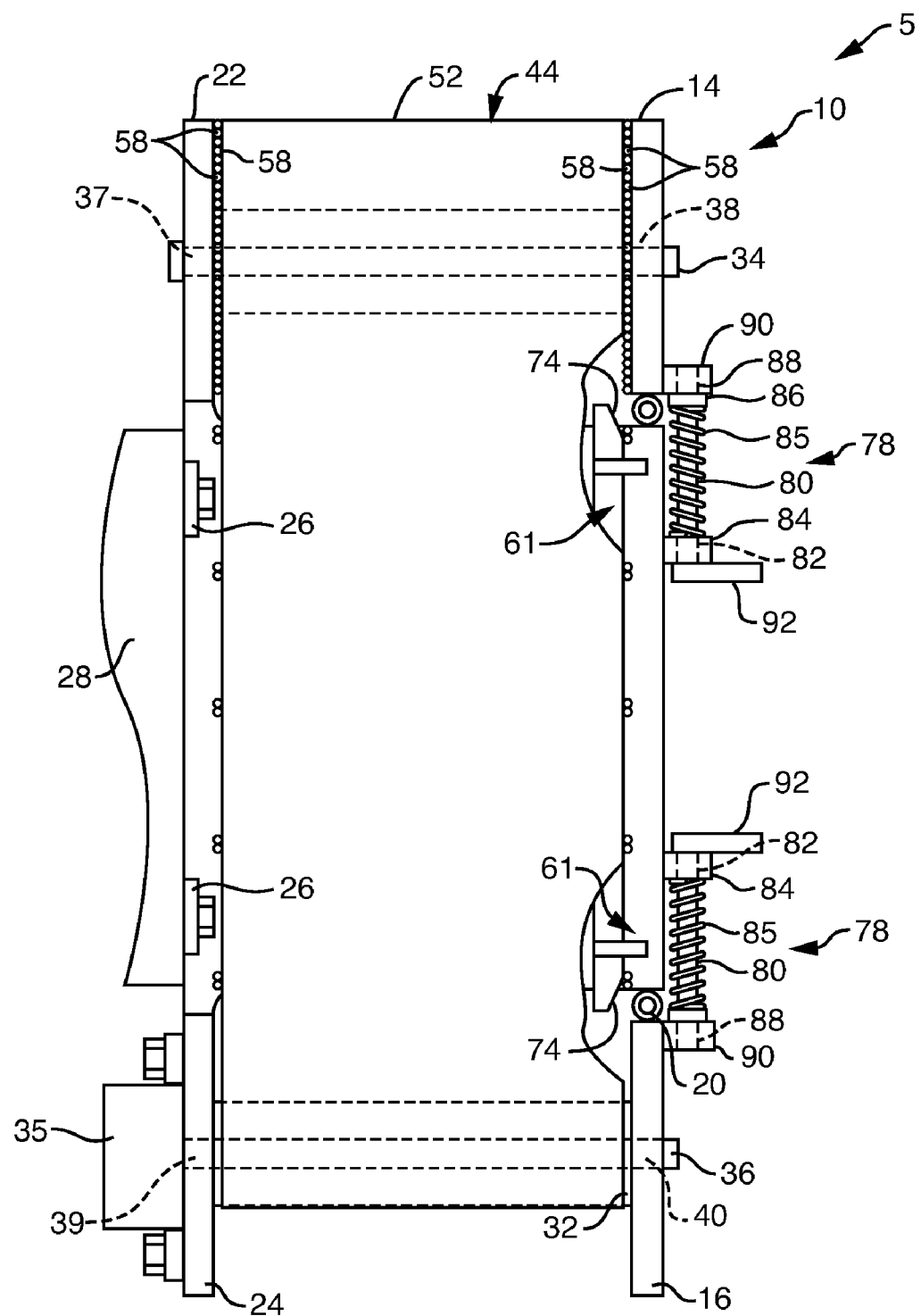
FIG. 3 is a side elevational view of the glove dispenser system, looking in the direction of arrow 3 in FIG. 1.
Figure 4:
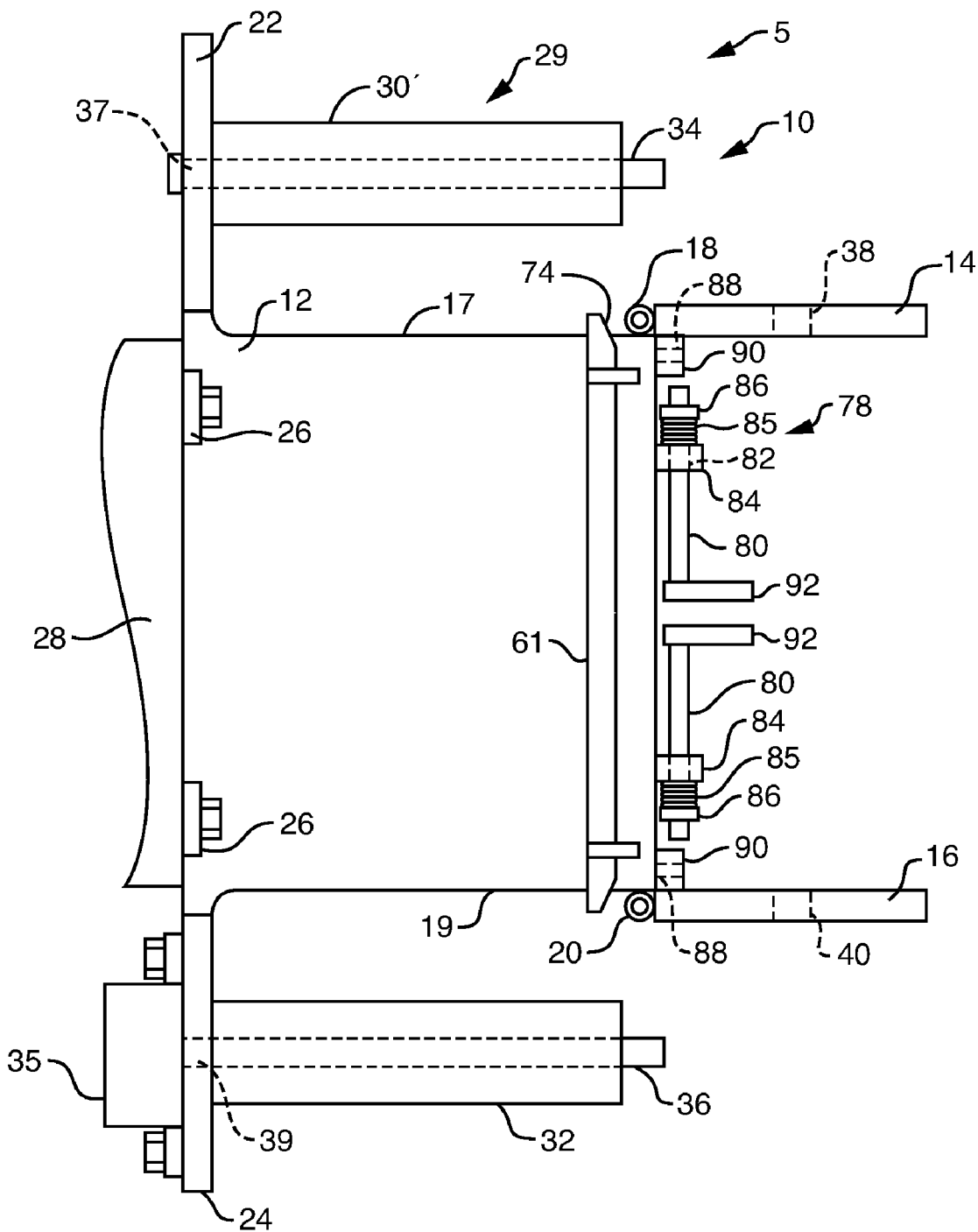
FIG. 4 is a side elevational view of the dispenser in a glove bearing sheet loading mode.

Referring particularly to FIGS. 2-4, each of the forward upper and lower flanges 14 and 16 can be maintained in their vertical operating (i.e., closed) positions by a latching mechanism, generally indicated by the reference numeral 78. Each latching mechanism 78 includes a rod 80 that extends through an aperture 82 of a forwardly extending block 84 that is fixed to the housing 12. The outer end of the rod 80 extends into an aperture 88 of a forwardly extending block 88 that is fixed to the corresponding forward flange. A compression spring 85 extends from block 84 to a washer 86 fixed to the rod 80 for maintaining the rod in the aperture 88. The inner end of the rod 80 is fixed to a handle 92 for manually pulling the outer end of the rod 80 out of the aperture 88. The removal of rods 80 from blocks 90, as shown in FIG. 4, enables the flanges 14 and 16 to be pivoted on hinges 18 and 20 to a horizontal orientation. This enables cores 46 and 48 to be inserted onto or removed from spindles 30 and 32, respectively.

As indicated above, the glove dispenser 10 includes a pair of glove opening mechanisms 60, 60'. Each glove opening mechanism 60, 60' is disposed on opposing lateral sides of the housing 12. In one arrangement, the glove opening mechanism 60, 60' are located external to the housing such that the glove opening mechanism 60, 60' are not covered by the housing 12. Such a configuration of the glove dispenser 10 allows a user to view the gloves 54 as he dons them to provide visual feedback to the user regarding placement of the user's hands within open gloves 54. Such visual feedback allows the glove dispenser 10 to be easily used and limits the ability for the user to insert his hand within a glove 54 such that the user's fingers and the fingers of the glove 54 are misaligned. Additionally, such location of the glove opening mechanism 60, 60' relative to the housing minimizes contamination of the glove dispenser 10 (e.g., build-up of food particles if used in the food industry) and provides user accessibility to the glove opening mechanism 60, 60' for maintenance of the glove dispenser 10.

Figure 1:
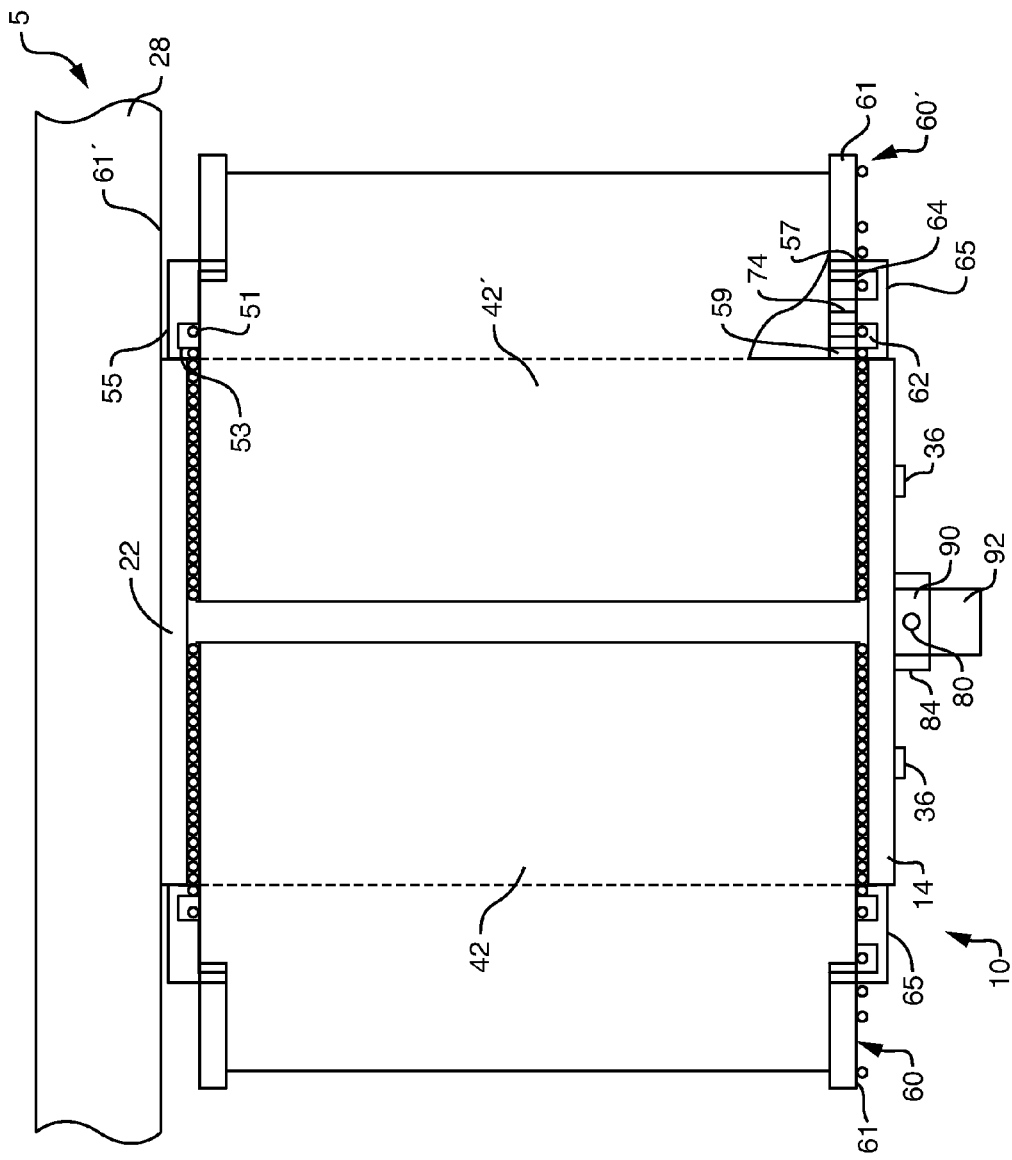
FIG. 1 is a top plan view of a glove dispenser system, according to one embodiment of the invention.

With reference to the glove opening mechanism 60' shown in FIGS. 1 and 2, the glove opening mechanism 60' includes a first structure 61 disposed at a front or proximal portion of the housing 12 and a second structure 61' disposed at a rear or distal portion of the housing 12 and opposing the first structure 61. In one arrangement, the first structure 61 includes a first support 57 and a second support 59 secured to each other by a bracket 65. With respect to the first structure 61, the first support 57 is constructed and arranged to receive the leading edge 104 of the first sheet portion 50 (e.g., beads 58A) while the second support 59 is constructed and arranged to receive the leading edge 108 of the second sheet portion 50 (e.g., beads 58B). While the first and second supports 57, 59 can be configured in a variety of ways, in one arrangement, the first support 57 defines a slot or support channel 64 extending from an entrance opening 68 to an exit opening 72 while the second support 59 defines a slot or support channel 62 extending from an entrance opening 66 to an exit opening 70. In one arrangement, each of the entrance openings 66 and 68 has an upwardly and rearwardly slanting guide surface 74, shown most clearly in FIGS. 1, 3 and 4, to easily receive either the leading edge 104, 108 of the glove bearing sheet 42.

In one arrangement, the second structure 61' includes a third support 55 that is constructed and arranged to receive the trailing edges 106, 110 of the first and second sheet portions 50, 52 (e.g., beads 58A' and 58B'). While the third support 55 can be configured in a variety of ways, in one arrangement, the third support 55 defines a slot or support channel 53 extending from an entrance opening 51 to an exit opening (not shown).

The first and second supports 57, 59 define a geometry that, in use, causes a glove 54 to be opened and presented to a user. For example, the first and second supports 57, 59 define a first neck portion 115 constructed and arranged to receive the first and second leading edges of the glove bearing sheet. The first and second supports 57, 59 also define a bifurcated opening portion 117 that forms a substantially circular geometry. The bifurcated opening portion is constructed and arranged to receive the first and second leading edges of the glove bearing sheet 42 from the first neck portion 115 and position the first and second leading edges of the glove bearing sheet 42 from the substantially closed position to the substantially open position to open at least a cuff portion of the glove 54. The first and second supports 57, 59 also define a second neck portion 119 that is constructed and arranged to receive the spent glove bearing sheet from the opening portion 117. The inner and outer slots 62 and 64, respectively, follow this geometry and gradually diverge from entrance openings 66 and 68 and then gradually coverage to exit openings 70 and 72, as shown most clearly in FIG. 2. In such a configuration, the glove opening apparatus 60 secures the glove bearing sheet 42 within the glove dispenser 10 to minimize or prevent inadvertent removal of the glove bearing sheet 42 from the glove dispenser 10. Also with such a configuration, the glove opening apparatus 60 orients the gloves relative to the glove dispenser 10 such that a longitudinal axis 122 of each glove 54 is substantially parallel to a support or base 120 on which the glove dispensing system 5 is disposed.

In use, and referring first to FIG. 4, the glove dispenser 10 is utilized by pivoting flanges 14 and 16 to the horizontal or load position. Glove bearing sheets 42, 42' wrapped around corresponding tubular cores 46, 46' are loaded onto each upper spindle 30, 30' while tubular cores 48, 48' are disposed on each lower spindle 32, 32'. While both upper spindles 30, 30' include glove bearing sheets 42, 42', for simplicity, the description of the loading of the glove bearing sheet 42' into operational positioning will be described. It should be understood that the described process can be used to load the glove bearing sheet 42 into operational positioning as well. Referring to FIG. 2, a free end of the glove bearing sheet 42' is pulled from the sheet 42' to the glove opening apparatus 60. The leading edge 104 (e.g., beads 58A) of the first sheet portion 50 is inserted into the slot 64 of the first support 57 and the leading edge 108 (e.g., beads 58B) of the second sheet portion 52 is inserted into the slot 62 of the second support 59. The trailing edges 106, 110 of the first and second sheet portions are inserted into the slot 53 of the third support 55.

The free end of the glove bearing sheet 42' is then drawn along the entire length of slots 62 and 64 and through the outlet openings 70 and 72 to the core 32'. A strip of adhesive is located on an inner side of the inner sheet 52 and is covered by a strip of release paper. The release paper is removed to expose the strip of adhesive which enables the inner sheet 52 to be fixed to the lower core 48'. The outer sheet 50 also has a strip of adhesive located on the inner side of the outer sheet and is covered by a strip of release paper. The removal of the release paper from the outer sheet 50 enables the outer sheet 50 to be fixed to the inner sheet 52. The outer sheet 50 can also be connected to the core 48 by making the leading end of the outer sheet 50 longer than the leading end of the inner sheet 52. With the sheets 50 and 52 secured to the core 48, the glove sheet advancement mechanism 35 is activated to draw the glove bearing sheet 42' through both glove opening mechanisms 60' and wind spend glove bearing sheet material onto the cores 48'.

After this initial start-up phase of the operation, ant turning attention to both the glove bearing sheets 42, 42' continued activation of the glove sheet advancement mechanism 35 causes a first glove 54 of the glove bearing sheets 42, 42' to be brought into the corresponding glove opening mechanism 60, 60'. As the leading edges 104, 108 (e.g., beads 58A and 58B) move downwardly along slots 64 and 62, respectively, and as the trailing edges 106, 110 move downwardly along slot 53 the leading edges 104, 108 diverge from each other as shown in FIG. 2 while the trailing edges 106, 110 are held in proximity to each other. For each glove opening mechanism 60, 60', this causes the outer sheet 50 to separate from the inner sheet 52, thereby causing the cuff end of the glove 54 to open, as illustrated in FIG. 2, such that the opening tapers from the cuff portion to the fingertip portion of the glove. This enables the operator to insert his or her hands into the open gloves and to pull the gloves out of the opening mechanism 60. The glove sheet advancement mechanism 35 is then deactivated and the glove dispenser 10 is ready for a subsequent advance of the glove bearing sheets 42, 42' and the consequent opening of a second pair of gloves 54.

While various embodiments of the invention have been particularly shown and described, it will be understood by those skilled in the art that various changes in form and details may be made therein without departing from the spirit and scope of the invention as defined by the appended claims.

For example, it would be possible to include a sprocket or other friction or locking system as part of the glove dispensing system 5, so that, when the user is donning the gloves, the inner and outer sheets 50, 52 are locked in position, so that the sheets 50, 52 do not unroll as the user is donning the gloves.

As indicated above, the glove dispensing system 5 includes a glove sheet receiver assembly 31 configured to receive the remnants of the glove bearing sheet 42 (e.g., the first and second sheets 50, 52) once a user has removed a glove 54 from the glove bearing sheet 42. Such description is by way of example only. In one arrangement, as an alternative to the re-rolling of the expended glove carrier sheets, the expended sheets are directed to accumulate in a bin or other receptacle.

As indicated above, the glove dispenser can be disposed on a base or support surface, such as a counter top, in a non-connected manner. Such description is by way of example only. In one arrangement, the housing 12 is secured to a structure, such as a wall. For example, a rearward portion 25 of the housing 12 includes a plurality of laterally extending flanges 26 for mounting the housing 12 to an appropriate supporting structure 28.

Figure 6:
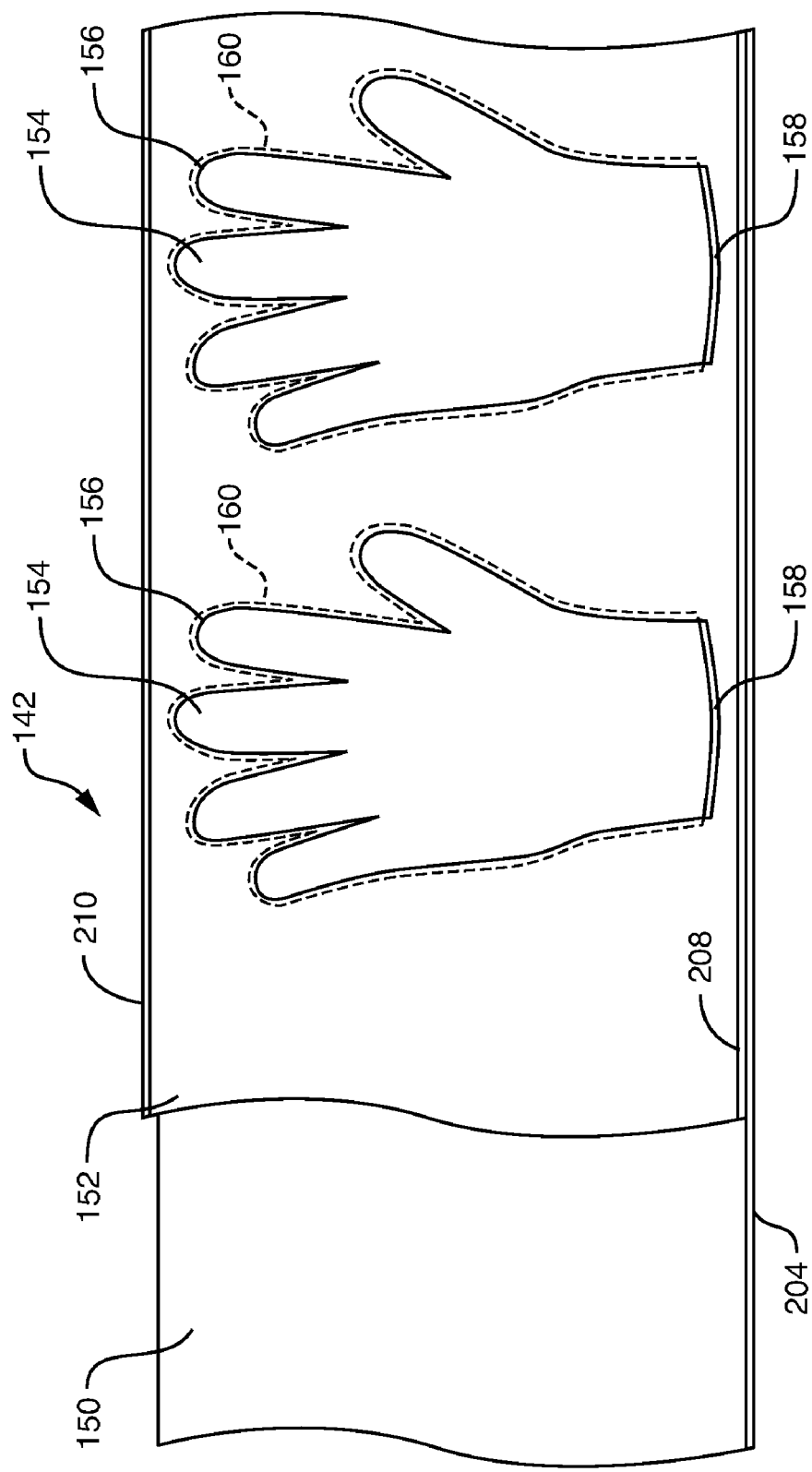
FIG. 6 illustrates an embodiment of a glove bearing sheet adapted for use with the dispenser of FIG. 1.

Also as indicated above the glove bearing sheet 42 includes a plurality of spaced gloves 54, such as formed from a plastic or latex material, disposed between a first sheet portion (e.g. inner sheet) 50 and a second sheet portion (e.g., outer sheet) 52 where each glove 54 is releasably connected to the first and second sheet portions 50, 52, such as by adhesive 56 for example. Such description is by way of example only. In one arrangement of a glove bearing sheet 142, as shown in FIG. 6, the gloves 154 are integrally and removeably formed as part of first and second sheet portions 150, 152. For example, as illustrated, the first sheet portion 150 overlies the second sheet portion 152. To form the gloves 154, such as using a heat sealing process, a manufacturer seals the first sheet portion 150 to the second sheet portion 152 such that the seal forms a glove shape 156 and such that a cuff end 158 of each glove 154 remains unsealed. The manufacturer then forms a series of perforations 160 within the first and second sheet portions 150, 152 about the glove shaped seal 160 for each of the gloves 154. In such an arrangement, in use, as the glove opening mechanism 60 separates the first and second sheet portions 150, 152 from each other, the glove opening mechanism 60 causes the cuff end 158 of the glove 154 to open. Once a user has inserted his hand into an open glove 154, the user can flex his fingers (i.e., make a fist) to separate the glove 154 from the glove bearing sheet 142 along the perforation 160.

Returning to FIG. 5, the first sheet portion 50 of the glove bearing sheet 42 has a first leading edge 104, that includes beads 58A, and a first trailing edge 106, that includes beads 58A' while the second sheet portion 52 of the glove bearing sheet 42 includes a second leading edge 108, that includes beads 58B and a second trailing edge 110, that includes beads 58B'. Such description is by way of example only. Returning to FIG. 6, the glove bearing sheet 142 includes the first sheet portion 150 having a first leading edge 204 formed as substantially continuous protrusion of material and the second sheet portion 152 having a second leading edge 204 formed as substantially continuous protrusion of material. The first and second sheet portions 150 of the glove bearing sheet 142 can be joined to form a single trailing edge 210 formed as a substantially continuous protrusion of material.

What is claimed is:

1. A glove dispensing system, comprising:
a housing;
a glove bearing sheet carried by the housing, the glove bearing sheet having:
a first sheet portion and a second sheet portion, the first sheet portion overlying the second sheet portion, the first sheet portion defining a first leading edge at a first end of the glove bearing sheet and the second sheet portion defining a second leading edge at the first end of the glove bearing sheet, and the first and second sheet portions defining a trailing edge at a second end of the glove bearing sheet, the first end of the glove bearing sheet opposing the second end of the glove bearing sheet, and
a glove carried by the glove bearing sheet between the first and second leading edges and the trailing edge such that a cuff portion of the glove is disposed in proximity to the first and second leading edges and such that a set of fingertip portions of the glove extend toward the trailing edge, the glove being removeably attached to the glove bearing sheet; and
a glove opening mechanism coupled to the housing, the glove opening mechanism being constructed and arranged to (i) receive the first and second leading edges of the glove bearing sheet and position the first and second leading edges of the glove bearing sheet from a substantially closed position to a substantially open position to open at least the cuff portion of the glove and (ii) receive the trailing edge of the glove bearing sheet to maintain the glove bearing sheet within the glove dispensing system;
wherein the glove is integrally and removeably formed as part of the first sheet portion and the second sheet portion of the glove bearing sheet;
the glove includes a glove shaped seal that secures the first sheet portion and the second sheet portion; and
the first sheet portion and the second sheet portion define a series of frangible members disposed in proximity to the glove shaped seal, wherein the series of frangible members are constructed and arranged to allow removal of the glove from the glove bearing sheet.

2. The glove dispensing system of claim 1, wherein the glove opening mechanism comprises:
a first support disposed at a proximal end of the housing and a second support disposed at the proximal end of the housing, the first support disposed in a spaced relationship relative the second support, the first support being constructed and arranged to receive the first leading edge of the glove bearing sheet and the second support being constructed and arranged to receive the second leading edge of the glove bearing sheet; and
a third support disposed at a distal end of the housing, the third support opposing the first support and the second support, the third support being constructed and arranged to receive the trailing edge of the glove bearing sheet.

3. The glove dispensing system of claim 2, wherein:
the glove bearing sheet comprises a first leading edge protrusion disposed at the first leading edge defined by the glove bearing sheet, a second leading edge protrusion disposed at the second leading edge defined by the glove bearing sheet, and a trailing edge protrusion disposed at the trailing edge of the glove bearing sheet;
the first support defines a first support channel constructed and arranged to receive the first leading edge protrusion;

the second support defines a second support channel constructed and arranged to receive the second leading edge protrusion; and the third support defines a third support channel constructed and arranged to receive the trailing edge protrusion.

4. The glove dispensing system of claim 2, wherein the first support and the second support define:

a first neck portion of the glove opening assembly, the first neck portion being constructed and arranged to receive the first and second leading edges of the glove bearing sheet;

an opening portion of the glove opening assembly, the opening portion defining a substantially circular geometry and being constructed and arranged to receive the first and second leading edges of the glove bearing sheet from the first neck portion and position the first and second leading edges of the glove bearing sheet from the substantially closed position to the substantially open position to open at least the cuff portion of the glove; and a second neck portion of the glove opening assembly, the second neck portion being constructed and arranged to receive the spent glove bearing sheet from the opening portion of the glove opening assembly.

5. The glove dispensing system of claim 1, comprising a glove sheet receiver assembly supported by the housing, the glove sheet receiver assembly being constructed and arranged to collect the glove bearing sheet received from the glove opening mechanism.

6. The glove dispensing system of claim 1, wherein the glove opening mechanism is disposed external relative to the housing.

7. The glove dispensing system of claim 1, wherein the glove opening mechanism is constructed and arranged to position the glove bearing sheet such that a longitudinal axis of the glove of the glove bearing sheet is substantially parallel to a support surface on which the housing is disposed.

8. The glove dispensing system of claim 1, comprising a sheet advancement mechanism constructed and arranged to advance glove bearing sheet relative to the glove opening mechanism such that glove is positioned from a closed to open position.

9. A glove bearing sheet for use with a glove dispenser, the glove bearing sheet having:

a first sheet portion and a second sheet portion, the first sheet portion overlying the second sheet portion, the first sheet portion defining a first leading edge at a first end of the glove bearing sheet and the second sheet portion defining a second leading edge at the first end of the glove bearing sheet, and the first and second sheet portions defining a trailing edge at a second end of the glove bearing sheet, the first end of the glove bearing sheet opposing the second end of the glove bearing sheet, and a glove integrally and removeably formed as part of the first sheet portion and the second sheet portion of the glove bearing sheet between the first and second leading edges and the trailing edge such that a cuff portion of the glove is disposed in proximity to the first and second leading edges with a set of fingertip portions of the glove extending toward the trailing edge;

the glove includes a glove shaped seal that secures the first sheet portion and the second sheet portion; and the first sheet portion and the second sheet portion define a series of frangible members disposed in proximity to the glove shaped seal, wherein the series of frangible members are constructed and arranged to allow removal of the glove from the glove bearing sheet.

10. The glove bearing sheet of claim 9, wherein the glove bearing sheet comprises a first leading edge protrusion disposed at the first leading edge defined by the glove bearing sheet a second leading edge protrusion disposed at the second leading edge defined by the glove bearing sheet.

11. The glove bearing sheet of claim 10, wherein at least one of the first leading edge protrusion and the second leading edge protrusion being configured as a substantially continuous protrusion extending along a length of the glove bearing sheet.

12. The glove bearing sheet of claim 10, wherein at least one of the first leading edge protrusion and the second leading edge protrusion being configured as a substantially discontinuous protrusion extending along a length of the glove bearing sheet.

13. The glove bearing sheet of claim 9, wherein the glove bearing sheet comprises a trailing edge protrusion disposed at the trailing edge of the glove bearing sheet.

14. The glove bearing sheet of claim 13, wherein the trailing edge protrusion is configured as a substantially continuous protrusion extending along a length of the glove bearing sheet.

15. The glove bearing sheet of claim 13, wherein the trailing edge protrusion is configured as a substantially discontinuous protrusion extending along a length of the glove bearing sheet.

16. The glove dispensing system of claim 1, wherein the glove bearing sheet comprises a first leading edge protrusion disposed at the first leading edge defined by the glove bearing sheet a second leading edge protrusion disposed at the second leading edge defined by the glove bearing sheet.

17. The glove dispensing system of claim 1, wherein the glove bearing sheet comprises a trailing edge protrusion disposed at the trailing edge of the glove bearing sheet.

18. A glove dispensing system, comprising:

a housing;

a glove bearing sheet carried by the housing, the glove bearing sheet having:

a first sheet portion and a second sheet portion, the first sheet portion overlying the second sheet portion, the first sheet portion defining a first leading edge at a first end of the glove bearing sheet and the second sheet portion defining a second leading edge at the first end of the glove bearing sheet, and the first and second sheet portions defining a trailing edge at a second end of the glove bearing sheet, the first end of the glove bearing sheet opposing the second end of the glove bearing sheet, and a glove carried by the glove bearing sheet between the first and second leading edges and the trailing edge such that a cuff portion of the glove is disposed in proximity to the first and second leading edges and such that a set of fingertip portions of the glove extend toward the trailing edge, the glove being removeably attached to the glove bearing sheet the glove bearing sheet comprises a first leading edge protrusion disposed at the first leading edge defined by the glove bearing sheet, a second leading edge protrusion disposed at the second leading edge defined by the glove bearing sheet, and a trailing edge protrusion disposed at the trailing edge of the glove bearing sheet;

the glove includes a glove shaped seal that secures the first sheet portion and the second sheet portion; and the first sheet portion and the second sheet portion defines a series of perforations disposed in proximity to the glove shaped seal, wherein the series of perforations are constructed and arranged to allow removal of the glove from the glove bearing sheet; and a glove opening mechanism carried by the housing, the glove opening mechanism comprising a first support disposed at a proximal end of the housing, a second support disposed at the proximal end of the housing, a third support disposed at a distal end of the housing, the third support opposing the first support and the second support, the first support defining a first support channel constructed and arranged to receive the first leading edge protrusion of the glove bearing sheet, the second support defining a second support channel constructed and arranged to receive the second leading edge protrusion of the glove bearing sheet, and the third support defining a third support channel constructed and arranged to receive the trailing edge protrusion of the glove bearing sheet, the first support and the second support being constructed and arranged to position the first and second leading edges of the glove bearing sheet from a substantially closed position to a substantially open position to open at least the cuff portion of the glove and the third support being constructed and arranged to maintain the glove bearing sheet within the glove dispensing system.

* * * * *